United States Patent
Blitzer et al.

(10) Patent No.: US 9,186,129 B2
(45) Date of Patent: Nov. 17, 2015

(54) EXPANDABLE DEVICE FOR TISSUE COLLECTION FROM AN AERODIGESTIVE BODY LUMEN

(75) Inventors: Andrew Blitzer, New York, NY (US); Marshall Strome, New York, NY (US)

(73) Assignee: ADN International, LLC, New York, NY (US)

( * ) Notice: Subject to any disclaimer, the term of this patent is extended or adjusted under 35 U.S.C. 154(b) by 226 days.

(21) Appl. No.: 14/122,372

(22) PCT Filed: May 25, 2012

(86) PCT No.: PCT/US2012/039577
§ 371 (c)(1),
(2), (4) Date: Feb. 18, 2014

(87) PCT Pub. No.: WO2012/162610
PCT Pub. Date: Nov. 29, 2012

(65) Prior Publication Data
US 2014/0171828 A1 Jun. 19, 2014

Related U.S. Application Data

(60) Provisional application No. 61/490,389, filed on May 26, 2011.

(51) Int. Cl.
*A61B 10/00* (2006.01)
*A61B 10/04* (2006.01)
(Continued)

(52) U.S. Cl.
CPC .............. *A61B 10/04* (2013.01); *A61B 5/4839* (2013.01); *A61B 5/6853* (2013.01); *A61B 10/02* (2013.01); *A61B 17/320725* (2013.01);
*A61B 18/24* (2013.01); *A61M 5/007* (2013.01); *A61B 2010/0216* (2013.01); *A61M 2025/105* (2013.01)

(58) Field of Classification Search
CPC ....... A61B 10/04; A61B 17/56; A61M 25/10; A61M 25/1002; A61M 25/104; A61M 25/1038; A61F 2/958
USPC ......................................... 600/562, 569, 572
See application file for complete search history.

(56) References Cited

U.S. PATENT DOCUMENTS

| 3,664,328 A | 5/1972 | Moyle, Jr. et al. |
| 4,735,214 A | 4/1988 | Berman |

(Continued)

FOREIGN PATENT DOCUMENTS

WO WO 94/23787 A1 10/1994

OTHER PUBLICATIONS

Anandasabapathy et al., Computer-assisted brush-biopsy analysis for the detection of dysplasia in a high-risk Barrett's esophagus surveillance population. Dig Dis Sci. Mar. 2011;56(3):761-6. doi: 10.1007/s10620-010-1459-z. Epub Oct. 27, 2010.

(Continued)

*Primary Examiner* — Brian Szmal
(74) *Attorney, Agent, or Firm* — Wolf, Greenfield & Sacks, P.C.

(57) ABSTRACT

A device for obtaining tissue from the aerodigestive tract is provided. The device may have internal and external folds and a tissue collection surface for collecting a tissue sample from a body lumen, such as the nose or throat. The present invention is also directed to methods of collecting a tissue sample using the devices, described herein.

13 Claims, 8 Drawing Sheets

(51) Int. Cl.
*A61B 10/02* (2006.01)
*A61B 5/00* (2006.01)
*A61B 18/24* (2006.01)
*A61M 5/00* (2006.01)
*A61B 17/3207* (2006.01)
*A61M 25/10* (2013.01)

(56) References Cited

U.S. PATENT DOCUMENTS

| | | | |
|---|---|---|---|
| 5,409,012 A | 4/1995 | Saharjian | |
| 5,509,899 A | 4/1996 | Fan et al. | |
| 5,533,516 A | 7/1996 | Sahatjian | |
| 5,599,298 A * | 2/1997 | Sahatjian | A61B 10/04 604/540 |
| 5,693,014 A * | 12/1997 | Abele et al. | A61M 25/1002 604/103.08 |
| 5,868,706 A | 2/1999 | Cox | |
| 6,475,164 B2 | 11/2002 | Gombrich et al. | |
| 6,544,224 B1 | 4/2003 | Steese-Bradley | |
| 6,685,671 B1 * | 2/2004 | Oishi et al. | A61M 25/10 604/27 |
| 7,108,661 B2 | 9/2006 | Secrest et al. | |
| 7,112,195 B2 | 9/2006 | Boll et al. | |
| 7,354,419 B2 | 4/2008 | Davies, Jr. et al. | |
| 7,803,149 B2 | 9/2010 | Bates et al. | |
| 7,815,687 B2 | 10/2010 | Bahler et al. | |
| 2002/0147458 A1 | 10/2002 | Hiblar | |
| 2004/0006355 A1 | 1/2004 | Vetter et al. | |
| 2005/0038383 A1 | 2/2005 | Kelley | |
| 2005/0070794 A1 | 3/2005 | Deal et al. | |
| 2006/0211019 A1 | 9/2006 | Halling et al. | |
| 2011/0190831 A1 * | 8/2011 | Mafi et al. | A61F 2/958 606/86 R |

OTHER PUBLICATIONS

Jhala et al., Gastrointestinal tract cytology. In: Atlas of Diagnostic Cytopathology. 2004. Atkinson et al., Eds. Chapter 5:1-5.

Johanson et al., Computer-assisted analysis of abrasive transepithelial brush biopsies increases the effectiveness of esophageal screening: a multicenter prospective clinical trial by the EndoCDx Collaborative Group. Dig Dis Sci. Mar. 2011;56(3):767-72. doi: 10.1007/s10620-010-1497-6. Epub Dec. 4, 2010.

Korsten et al., Balloon cytology in screening of asymptomatic alcoholics for esophageal cancer, Part I. Dig Dis Sci. Sep. 1985;30(9):845-51.

[No Author Listed]. Esophageal Cancer Screening: Health Professional Version. National Cancer Institute. www.cancer.gov. Last modified Jul. 16, 2010. 5 pages.

Roth et al., Cytologic detection of esophageal squamous cell carcinoma and precursor lesions using balloon and sponge samplers in asymptomatic adults in Linxian, China. Cancer. Dec. 1, 1997;80(11):2047-59.

Saidi et al., Oesophageal cancer among the Turkomans of northeast Iran. Br J Cancer. Nov. 2000;83(9):1249-54.

* cited by examiner

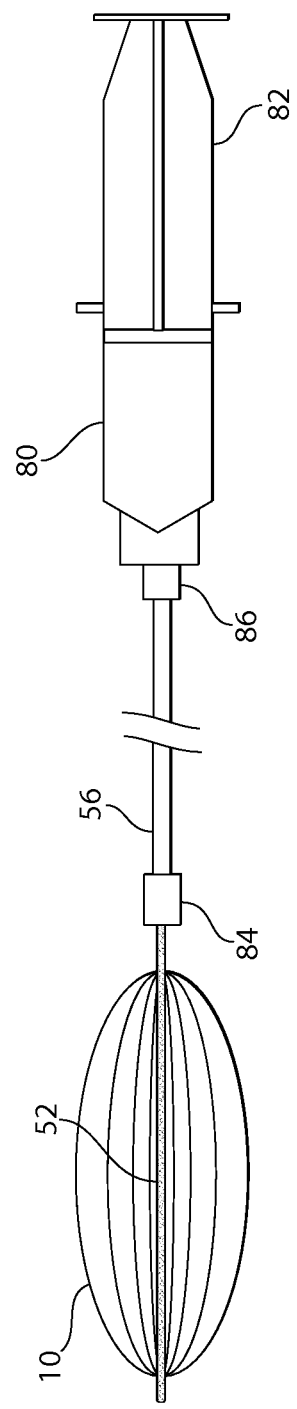

EXPANDABLE DEVICE FOR TISSUE COLLECTION FROM AN AERODIGESTIVE BODY LUMEN

RELATED APPLICATIONS

This application is a national stage filing under 35 U.S.C. §371 of international PCT application number PCT/US2012/039577, filed on May 25, 2012, which claims the benefit under 35 U.S.C. §119(e) of U.S. provisional application No. 61/490,389, filed May 26, 2011, the content of each of which is hereby incorporated by reference in its entirety.

FIELD OF THE INVENTION

The present invention relates to devices having internal and external folds and a tissue collection surface for collecting a tissue sample from a body lumen, such as the nose or throat. The present invention is also directed to methods of collecting a tissue sample using the devices, described herein.

BACKGROUND OF INVENTION

Current devices used for collecting from a body lumen (e.g., esophagus) a tissue sample suspected of disease have not provided adequate clinical sampling of the entire circumference of the lumen. This lack of circumferential sampling often leads to sampling errors. Additionally, such existing devices often cause the tissue sample from being contaminated by neighboring tissue collected en route to and from the site of the suspected diseased tissue.

SUMMARY OF INVENTION

A device and method for collecting tissue from an internal lumen is provided according to the invention. In certain aspects, provided herein are methods of collecting tissue from an individual, comprising: (a) advancing a deflated expandable device having internal and external folds and a tissue collection surface on one or more of the internal folds to a collection site within a body lumen of an individual; (b) expanding the expandable device at the collection site to unfurl at least some of the folds so that the tissue collection surface contacts tissue of the body lumen; (c) collecting tissue on the tissue collection surface of the expandable device; (d) contracting the expandable device; and (e) removing the contracted expandable device from the individual.

In certain embodiments, the body lumen is selected from the group consisting of pharynx, larynx, oropharynx, nasopharynx, nasal cavity, nose, throat, trachea, and esophagus.

In some embodiments, the step of collecting tissue involves rotating the expandable device.

In some embodiments, the expandable device is a balloon. In certain embodiments, the balloon is partially inflated at the collection site, while in other embodiments, the balloon is fully inflated at the collection site. In particular embodiments, the step of collecting tissue involves inflating and deflating the balloon. In some embodiments, the step of collecting tissue involves rotating the fully inflated balloon, whereas in other embodiments, the step of collecting cells involves moving the fully inflated balloon up and down.

In certain embodiments, according to the methods described herein, the contracted expandable device is removed from the individual without a stent or protective cover.

Other aspects provided herein are directed to an expandable device, comprising an outer surface sized to fit within a body lumen, one or more regions of the outer surface having a tissue collection surface, wherein when the expandable device is deflated the outer surface has internal folds and external folds, wherein the tissue collection surface is present on one or more internal folds of the outer surface and is not present on one or more external folds.

In certain embodiments, the device is a balloon. In some embodiments, the balloon is made of latex, silicone elastomer, butadiene/acrylonitride copolymers, copolyesters, ethylene vinylacetate (EVB) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, and styrene-ethylene/butylene-styrene, polyesters, polyolefins, polyamides, polyvinyl chloride, or a combination thereof. In certain embodiments, the balloon has one or more inflatable compartments. In some embodiments, the balloon has a shape selected from the group consisting of round, conical, oblong, and tissue specific. In some embodiments, the tissue specific shape is a shape that is an approximate mirror image of a body lumen.

In some embodiments, the tissue collection surface of the expandable device is an abrasive surface. The abrasive surface may be made of any abrasive, non-toxic material. In particular embodiments, the abrasive surface is a coating of particulate. In certain embodiments, the particulate is made of silica, a biocompatible plastic, a biopolymer (e.g., polycaprolactone (PCA), polyhydroxyalkanoate (PHA), polyhydroxybutanoate (PHB), or polyhydroxybutyrate-valerate (PHBV)), or a combination thereof.

In other embodiments, the tissue collection surface is on alternating internal folds. In particular embodiments, the tissue collection surface forms a pattern on the outer surface of the inflated expandable device. In some embodiments the tissue collection surface is not present on any external folds, and in other embodiments the tissue collection surface is present on all internal folds.

In certain embodiments, the expandable device described herein has an expanded configuration and a contracted configuration, wherein the internal and external folds are pleated when the device is in the contracted configuration and unpleated when the device is in the expanded configuration. In certain embodiments, the folds are corrugated in the contracted configuration.

In some embodiments, the expandable device is attached to a tube or channel. In certain embodiments, an instrument is advanced through the tube or channel prior to contracting the expandable device. The instrument may be a laser fiber, a cytology brush, an applicator, a needle, forceps, or a blade. The tube or channel may be, for instance, an endoscope or part of an endoscope.

In some embodiments, an agent is delivered to the individual prior to contracting the expandable device. The agent can be delivered to the individual through the tube or channel, or the agent can be coated on the surface of the expandable device. In some embodiments, the agent is coated on the internal folds of the expandable device. In some embodiments, the agent can be a therapeutic agent, a diagnostic agent or an imaging agent.

Certain aspects described herein relate to a balloon cytology device, comprising: a balloon having an outer surface sized to fit within an esophagus, one or more regions of the outer surface having a tissue collection surface; and a support member having a proximal end region and a distal end region, wherein the support member is connected to the balloon at the distal end region and wherein the minimal length of the support member between the proximal end region and the distal end region is 10 cm, wherein the support member includes a hollow compartment for transferring a gas or liquid to the balloon to inflate the balloon.

Other aspects are directed to an apparatus, comprising: (a) a support member; and (b) an expandable device as described in any of the foregoing embodiments, wherein the expandable device is connected to the support member. In particular embodiments, the support member is made of a hydrogel, silicone, polyethylene, polypropylene, polyurethane, polycaprolactone, polytetrafluoroethylene (PTFE), copolymers, or a combination thereof. In some embodiments, the support member is a catheter or stylet. In certain embodiments, the support member has a proximal end region and a distal end region and the expandable device (e.g., balloon) is located at the distal end region. In some embodiments, the support member comprises a guide at the distal end region. In particular embodiments, the apparatus comprises a guide-wire.

In certain embodiments, the apparatus of any of the foregoing embodiments comprises an actuator at the proximal end region. In some embodiments, the actuator is a syringe.

In certain embodiments, the apparatus does not include a cover which covers part or all of the expandable device.

Still other aspects provided herein are directed to a kit, comprising: (a) the apparatus of any one of the foregoing embodiments; and (b) instructions or direction for obtaining instructions for using the apparatus. In certain embodiments, components (a) and (b) are arranged in a container.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

FIG. 5 schematizes one embodiment of a cytology collection apparatus, including an expandable device, support member, hose, and actuator (syringe).

DETAILED DESCRIPTION OF INVENTION

Figures 1, 1A:
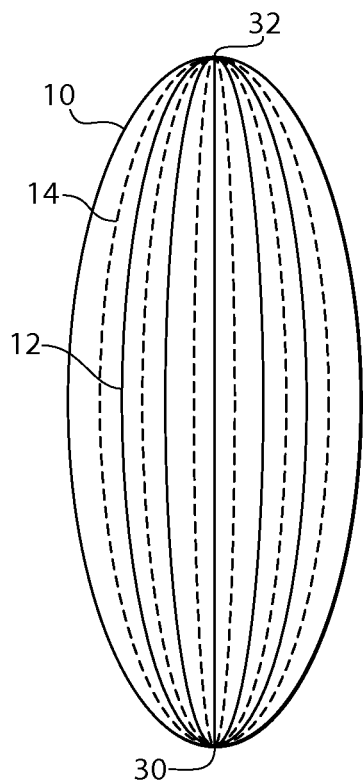
FIGS. 1A-1B schematize an embodiment of the expandable device: deflated, side view (FIG. 1A, left panel); deflated, top view depicted various fold configurations (FIG. 1A, right panel); inflated, side view (FIG. 1B, right panel); and inflated, top view (FIG. 1B, left panel).

Provided herein are methods and devices for collecting a tissue sample from a body such as a cylindrical lumen in the upper aerodigestive tract. The aerodigestive tract includes for instance, nasopharynx, nose, throat, airway, or esophagus. Obtaining tissue from the aerodigestive tract remains a technical challenge. A number of devices have been designed to achieve tissue sampling in this area of the body. However, the existing devices have many limitations. The devices of the invention provide a solution for the non-invasive sampling of tissue from this area of the body. Tissue sampling from cylindrical lumens is typically accompanied by some degree of sampling error, as it is difficult to collect cells from the entire circumference of, for example, an esophagus. By providing a device having the structural properties described herein and which expands to the walls of the lumen, it is possible to obtain a true sampling of the lumen.

The devices are expandable (e.g., inflatable) and generally have folded regions, at least some of which include a tissue collection surface for capturing the tissue once the device is expanded. The device is inserted into the aerodigestive tract and at the desired site of tissue collection, the device is expanded, such that the folds unfurl and are exposed to the tissue walls. The tissue collection surface on the now unfolded regions of the device is then allowed to contact the tissue. The tissue collection surface is configured in a way such that it is capable of dislodging the tissue from the tissue wall and capturing it on the surface. The device is then reduced or deflated such that the regions of the device having tissue collection surfaces are folded and face internal, such that they are no longer exposed to the tissue walls. The device may then be removed from the individual. As the device is being removed from the individual, the tissue collected using the device is protected from the body environment. Once the device is outside of the body the tissue can be removed from the tissue collection surface using any known methods in the art, for instance by using a buffered (e.g., PBS (phosphate buffered saline)) wash.

The expandable device described herein has an outer surface sized to fit within a cylindrical body lumen of an individual. A cylindrical body lumen, as used herein, refers to any space or cavity in the upper aerodigestive tract formed by a tubular or tubular-like organ. The term cylindrical is not used in this context to indicate a perfect cylindrical shape, but rather to indicate the tubular organs of the aerodigestive tract. A tubular or tubular-like organ is one that has an external surface forming a space or lumen positioned within the body but that is exposed to the outside of the body. For example, organs of the aerodigestive tract having a cylindrical body lumen include but are not limited to a nose or throat, including the pharynx, larynx, oropharynx, nasopharynx, nasal cavity, trachea, and esophagus of an individual. In a particular embodiment, the device is sized to fit within an esophagus of an individual.

An individual, as discussed herein, refers to a human. Preferably the human is a patient in need of cytological analysis.

The device of the invention is useful for collecting tissue from an individual. Tissue, as used herein, refers to a sample of material from a subject, including at least one cell. Preferably the tissue sample is composed primarily of cells that are obtained from the lumen of the individual. For instance, this may include epithelial cells or any cells present in a tumor or abnormal growth occurring in any of the foregoing body lumens.

The tissue may be removed from the expandable device using any methods known to those of skill in the art. The tissue samples can then be processed in a number of ways. For example the tissue may have been collected for the purpose of detecting the presence or absence of cancer cells in the tissue. A number of tumors of the head and neck are associated with the squamous epithelium of the mucosal lining in the nose and throat. Additionally, the cells lining the esophagus can develop into esophageal cancer. These and other cells can be sampled easily and effectively using the device of the invention to provide, for example, a cytology tool in routine examination, or a diagnostic tool in cancers or other abnormal growths of the upper aerodigestive tract.

In some instances, the tissue being sampled has a mucosal surface. It may be desirable to remove the mucous layer prior to (or at the same time) as tissue sampling. It is possible to achieve this by pretreating with or applying a mucolytic agent on the expandable device. Mucolytic agents include but are not limited to acetylcysteine, ambroxol, bromhexine, carbocisteine, domiodol, dornase alfa, eprazinone, erdosteine, letosteine, mesna, neltenexine, sobrerol, stepronin, and tiopronin.

The outer surface of the expandable device has a tissue collection surface. A tissue collection surface, as used herein refers to a region of the expandable device that is configured to capture tissue. It may be configured to capture tissue by having a charged or otherwise sticky surface. Alternatively or additionally, it is configured to capture tissue by having a rough surface that dislodges the tissue from the lumen. The configuration of the surface may be dictated by the types of materials used to produce or coat the surface as well as the shape of the material making up or coating the surface. Materials used in the preparation of the expandable device as well as the tissue collection surface are described in more detail below.

The tissue collection surface is positioned on the folds of the device such that when the device is expanded at the desired site in the body and the tissue collection surface contacts the walls of the lumen, the tissue collection surface will dislodge and capture tissue at the site at one or more contact points along the lumen. The tissue collection surface may contact only a portion of the lumen or alternatively may contact the entire circumference of the lumen. The contact between the tissue collection surface and the lumen results in a transfer of at least some tissue from the lumen to the tissue collection surface. In order to enhance the transfer of the tissue, the expandable device may be moved relative to the lumen. The movement may involve any range of motion that assists the transfer of the tissue to the tissue collection surface. For instance, the expandable device may be moved horizontally and/or vertically, or it may be rotated, as discussed in more detail below.

The expandable device also has some internal and external folds. The folds may be present when the device is deflated, and when the device is inflated the amount and extent of the folds are decreased. If the expandable device is completely inflated the appearance of the folds may be absent. It is desirable in some cases to have at least some of the tissue collection surface located on the internal folds. The tissue collection surface covers, in some embodiments, at least 50%, 60%, 70%, 80%, 90% or 95% of the internal folds. In other instances, the tissue collection surface covers 100% of the internal surfaces. In a deflated or partially deflated configuration the tissue collection surface on the internal folds would be protected from exposure to the lumen.

The folds may have any type of configuration or pattern. Types of folds include but are not limited to half fold, tri-fold, gate fold, Z fold, parallel fold, accordion fold, quarter fold, pleats, reverse folds, squash folds half/tri fold, and tri/half hold. FIG. 1 provides examples of an expandable device of the invention having pleat folds in a deflated configuration (FIG. 1A) and an inflated configuration (FIG. 1B). In FIG. 1 the expandable device 10 is shown from a side view (FIGS. 1A and 1B, left panels) and a top view (FIGS. 1A and 1B, right panels), such that the external folds 12 and internal folds 14 can be observed.

The number of internal folds on the expandable device may range from about two to about thirty. In some embodiments, the expandable device has at least two internal folds, while in other embodiments, it has at least ten internal folds. In yet other embodiments, the expandable device has at least fifteen or at least twenty internal folds, or more. In particular embodiments, the expandable device has more than 30 folds. The number of folds (internal and external) depends on the size and shape of the device, which depends on the size and shape of the body lumen in which the device is used. The shape of the device may be any shape as long as it is capable of collecting cells in an inflated state. The shape of the device may be, for instance, round, conical, or oblong. Alternatively, the shape of the device is tissue specific. For example, the device may approximately mirror the image of the cylindrical lumen (e.g., esophagus) from which the tissue sample is collected. The particular shape and dimensions of the expandable device may be selected as required for its specific purpose and for the particular tissue collection site at which it will be used. For example, expandable devices configured for introduction into the throat (e.g. esophagus or trachea) may have diameters of up to about 25 mm, or more. In some embodiments, the diameter of the device expands to about 10 to about 30 mm in diameter, while in other embodiments, the diameter of the device expands to about 15 to about 20 mm in diameter. The lengths of the expandable devices described herein vary widely, depending on the application. For example, the length of the expandable device can be up to about 100 mm, or more. In some embodiments, the expandable device is about 10 to about 100 mm, whereas in other embodiments, it is about 20 to about 50 mm in length.

Expandable, as used in the context of expandable device, refers to a material which is capable of being transitioned from a compact form (e.g., deflated) to an expanded form (e.g., inflated). Expandable devices useful according to the invention include but are not limited to balloons, balloon expandable collectors or self-expandable collectors. A balloon is an inflatable, flexible bag made of elastic or elastic-like (e.g., polymer-based elastic) that expands as it is filled with a gas, such as helium, hydrogen, nitrous oxide, oxygen, or air. When a balloon is expanded, typically the material from which the balloon is made (e.g., rubber, latex, polychloroprene, a nylon fabric) expands (stretches as a result of its elasticity).

A balloon expandable collector is a composite balloon and cover collection device such that when the balloon portion is inflated, the cover of the device contacts a lumen for tissue collection. An example of a balloon expandable collector is a non-balloon material covering a balloon. The non-balloon material may be physically attached, partially or fully, to the balloon or may unattached to the balloon.

A self-expandable collector is a self-expandable device that does not require inflation by a gas. For instance, the self-expandable collector may be a sac or pouch made of material that is not elastic or elastic-like (e.g., polymer-based elastic or memory metal such as nitinol) and is not necessarily stretched when the device is expanded. Alternatively it may be made of an elastic material that is constrained to a small size but which expands when deconstrained. In other embodiments, it may be a composite of materials, one of which having memory (e.g., nitinol or plastic spring). In certain embodiments, a self-expandable collector requires delivery by catheter or other cylindrical support structure. In such embodiments, the self-expandable device is positioned within the catheter as it is advanced to the tissue collection site, then deployed from the catheter to self-expand for tissue collection.

In certain embodiments, the expandable device may be made of latex, silicone elastomer, butadiene/acrylonitride copolymers, copolyesters, ethylene vinylacetate (EVB) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, and styrene-ethylene/butylene-styrene, polyesters, polyolefins, polyamides, polyvinyl chloride, or equivalent or combination thereof. Other materials are well known to the skilled artisan.

The tissue collection surface may be formed from the same material or from a different material than the other non-tissue collection surfaces of the expandable devices. In some embodiments, the tissue collection surface is an abrasive material (particulate). In particular embodiments, the abrasive surface is a coating of particulate. In certain embodiments, the particulate is made of silica, a biocompatible plastic, a biopolymer, or combinations thereof. Examples of biopolymers include polycaprolactone (PCA), polyhydroxyalkanoate (PHA), polyhydroxybutanoate (PHB), and polyhydroxybutyrate-valerate (PHBV). In some embodiments, the particulate is made of granules. In certain embodiments, the granular size of the particulate is about 5 to about 500 microns. In other embodiments, the granular size of the particulate is about 25, or about 50 microns. The thickness of the tissue collection surface may be the same as, thinner than, or thicker than the expandable device material. In some embodiments, the tissue collection surface is thicker than the device material. Even in such embodiments where the thickness of the tissue collection surface exceeds that of the device material, the tissue collection surface is protected from exposure to the environment by the folds of the device such that the tissue collection surface is not contaminated during protraction and retraction of the device.

The tissue collection surface may form a pattern, for example, a horizontal or vertical pattern. A pattern may be an organized or random arrangement of the abrasive particulate.

Depending on the device and the purpose of the device, the tissue collection surface is present on at least one of the internal folds. For instance, the tissue collection surface may be on a single internal fold, all internal folds, alternating internal folds or any combination thereof. The tissue collection surface may be present on at least 50%, 60%, 70%, 80%, 90% or 95% of the internal folds. In some embodiments, the tissue collection surface is on 100% of the internal folds.

Figure 2A:
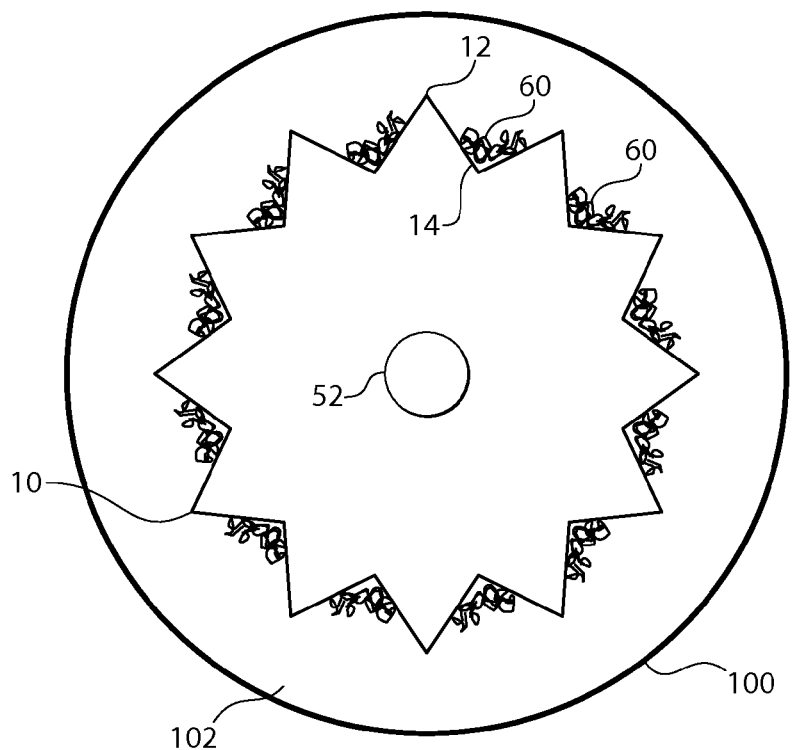
FIGS. 2A-2B schematize an embodiment of the device, deflated within a body lumen (FIG. 2A), and inflated within a body lumen (FIG. 2B).
Figure 2B:
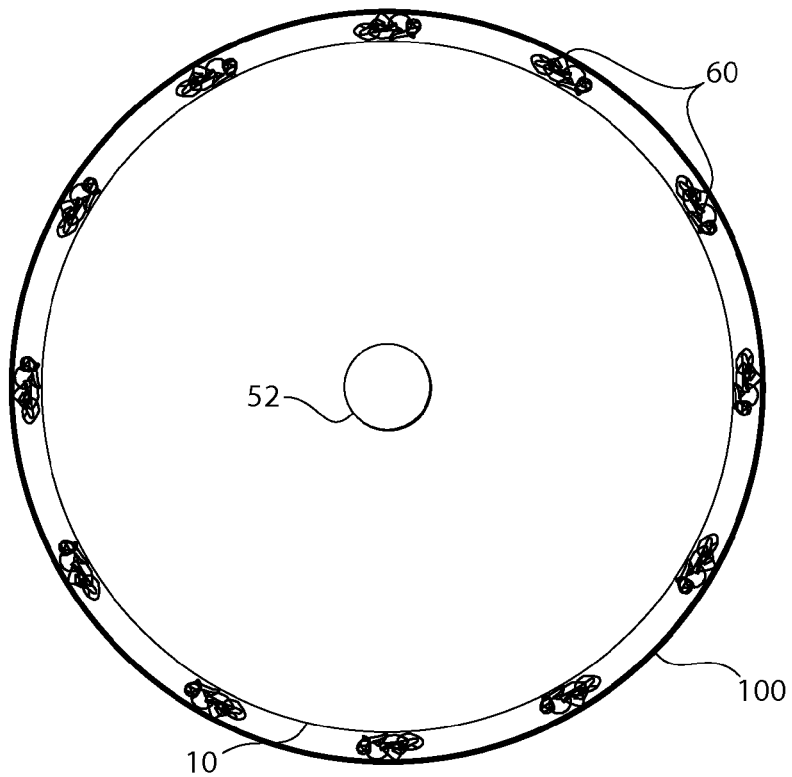

The tissue collection surface may also be present on some of the external folds. For instance the tissue collection surface is present on less than 40%, 30%, 20%, 10%, 5%, or 1% of the external folds. In some embodiments the tissue collection surface is absent altogether from the surface of the external folds. An example of a configuration having the tissue collection surfaces present on all the internal folds and not on any of the external folds is shown in FIG. 2B. In such embodiments, when the device is inflated within a body lumen, the tissue collection surfaces 60 of the internal folds 14 are exposed and contact the wall of the lumen (FIG. 2B), but when the device is deflated the tissue collection surface is retracted and protected from subsequent contact with the walls of the lumen (FIG. 2A). In this way, the collected tissue sample does not become contaminated with neighboring cells (and conversely the neighboring cells are not damaged) when the expandable device is removed from the body lumen.

The tissue collection surface may or may not be on any external folds. If it is desirable to collect cells from as many surfaces as possible the collection surface may be present on one or more external folds. By having tissue collection surfaces present on the external folds as well as the internal folds, the different sections of the device may be used to collect tissue from different areas of the body. For instance, the external folds will be exposed to the tissue as the device passes through different lumen. It is also exposed to the tissue at the specified collection area, where the device is expanded. When the device is removed from the patient the external folds having a tissue collection surface will have a mixture of cells from different tissues and the internal folds will only have cells from the tissue sampled while the device was expanded.

Alternatively, the tissue collection surface may also be present on an external surface under conditions when it is not desirable to collect cells outside of the target area. In this case, the device can be used with a protective cover. The expandable device may be placed inside the protective covering and advanced into a body lumen to a tissue collection site in this configuration. At the tissue collection site, the expandable device is deployed from the protective covering, and subsequently expanded, fully or partially, to contact the wall of the lumen. The tissue sample is collected, the device is contracted, retracted back into the protective covering, and then removed from the body lumen.

Figure 4A:
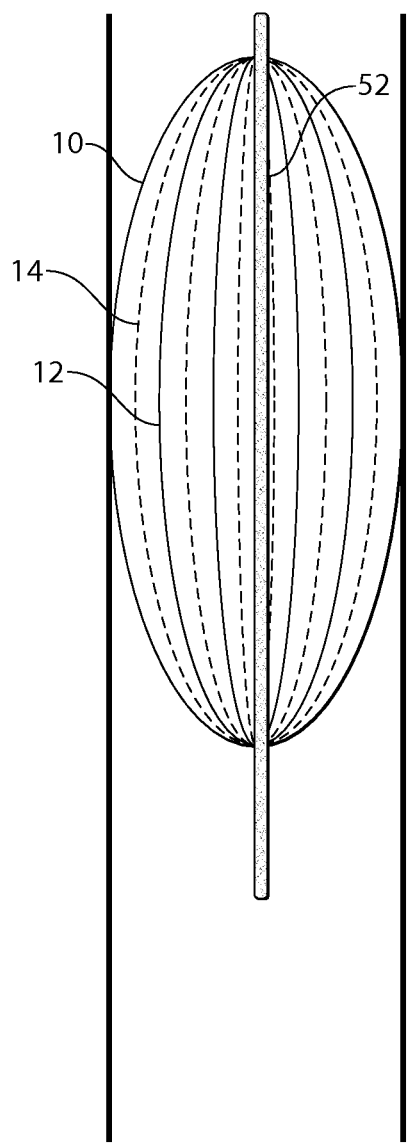
FIGS. 4A-4B schematize one embodiment of the expandable device having a protective covering.
Figure 4B:
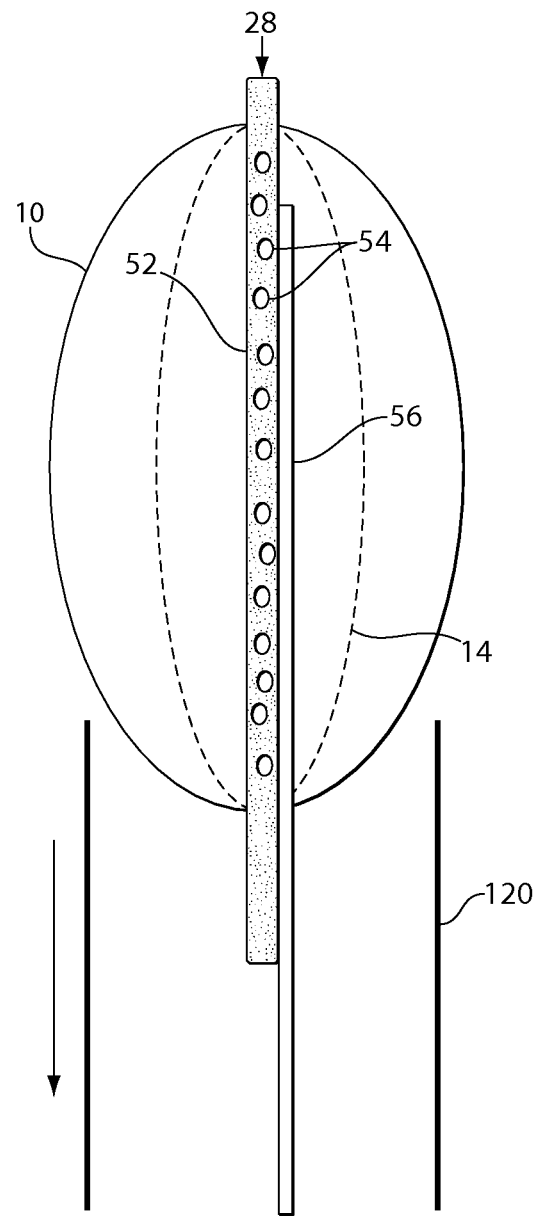

A protective cover, as used herein, refers to a structural element sized to enclose part or all of the expandable device, such that the expandable device is shielded from contact with surfaces. For instance, in FIG. 4, a protective cover 120 is placed over the expandable device 10 while the device is moved through the body to the region where tissue sampling will be achieved (FIG. 4A). The protective cover is then removed, and the expandable device is expanded to collect tissue (FIG. 4B). Once the tissue collection step is complete, the device is deflated, and the protective cover may be placed over the expandable device.

The protective cover may be made of a flexible material such that it may be folded back on itself or otherwise collapsed to expose the expandable device. Alternatively, it may be made from an inflexible material. In such a case it could simply be slid off the expandable device, or the expandable device could be moved out from the protective cover at the tissue collection area of the lumen.

In some embodiments, the protective cover is a tube, such as a catheter, plastic stylet, or other covering used to deliver a medical device to a body lumen. A protective cover may optionally be used with any configuration of expandable device described herein.

Alternatively, the expandable device may be attached to a tube or channel, through which an object such as equipment or an agent (e.g., therapeutic agent such as medicine) may be delivered. For example, an endoscope may be advanced through the tube to visualize the area around the area around the expandable device. Alternatively the tube or channel may be an endoscope or part of an endoscope. An endoscope is an instrument used to examine the interior of a hollow organ or cavity of the body. Typically, endoscopes are inserted directly into the organ. In some embodiments, an endoscope is comprised of a rigid or flexible tube, a light delivery system to illuminate the organ or object under inspection (the light source can be outside of the body and the light can be directed via an optical fiber system), a lens system that transmits an image (still or motion) to a viewer from an objective lens to the viewer (e.g., a relay lens system in the case of rigid endoscopes or a bundle of fiberoptics in the case of a fiberscope), and an eyepiece. In some embodiments, the endoscope is also attached to an additional tube or channel to allow entry of equipment such as medical instruments or manipulators.

In some embodiments, equipment is delivered through a tube or channel of the expandable device. Such equipment includes, but is not limited to, a laser fiber, a cytology brush, an applicator, a needle, forceps, and a blade.

Any one of the foregoing devices and embodiments may be used in a method of collecting cells from an individual, as described herein. Such methods include (a) advancing a deflated (contracted) expandable device having internal and external folds and a tissue collection surface on one or more of the internal folds to a collection site within a body lumen of an individual; (b) expanding (inflating) the expandable device at the collection site to unfurl at least some of the folds so that the tissue collection surface contacts tissue of the body lumen; (c) collecting tissue on the tissue collection surface of the expandable device; (d) contracting (deflating) the expandable device; and (e) removing the contracted expandable device from the individual.

In certain embodiments, collecting tissue involves rotating the fully expanded device. Rotating refers to making a circular movement around an imaginary center (rotation) axis. Rotating the device permits sloughing and subsequent collection of the tissue by the tissue collection surface. The device is considered to be fully expanded when the tissue collection surface contacts the wall of the lumen at the collection site. In other embodiments, collecting tissue involves moving the fully inflated device up and down (along the longitudinal axis of the lumen), such that motion permits sloughing and subsequent collection of the tissue by the tissue collection surface.

In some embodiments, the expandable device is delivered to the tissue collection site in the individual without a stent or protective cover. In other embodiments, however, a protective cover is used. For example, if the tissue collection device is on the external folds, then the device is delivered within a protective cover so that the tissue collection surface does not contact neighboring tissue en route to the tissue collection site.

It is also possible to use the device of the invention for the delivery of agents. Agents include, for instance, therapeutic agents, diagnostic agents, and imaging agents (e.g., labeled compounds). Therefore, the invention contemplates a device having an agent linked to the device. The agent may be coated on the surface of the expandable device, on the interior and/or exterior folds. Alternatively, the agent may be enclosed in a pouch or other enclosure that can be activated to open and release the agent.

The agents may be naturally occurring or non-naturally occurring. Naturally occurring agents include those capable of being synthesized by the subjects on whom the expandable device is used. Non-naturally occurring are those that do not exist in nature normally, whether produced by plant, animal, microbe or other living organism.

The agent may be without limitation a chemical compound including a small molecule, a protein, a polypeptide, a peptide, a nucleic acid, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form. The invention further contemplates the loading of more than one type of agent on the expandable device.

One class of agents is peptide-based agents such as (single or multi-chain) proteins and peptides. Examples include antibodies, single chain antibodies, antibody fragments, enzymes, co-factors, receptors, ligands, transcription factors and other regulatory factors, some antigens (as discussed below), cytokines, chemokines, hormones, and the like.

Another class of agents that can be delivered using the expandable device of the invention includes chemical compounds.

A variety of agents that are currently used for therapeutic or diagnostic purposes can be delivered according to the invention and these include without limitation imaging agents, immunomodulatory agents such as immunostimulatory agents and immunoinhibitory agents (e.g., cyclosporine), antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, analgesics, opioids, enzyme inhibitors, neurotoxins, hypnotics, anti-histamines, lubricants, tranquilizers, anti-convulsants, muscle relaxants, anti-Parkinson agents, anti-spasmodics, muscle contractants including channel blockers, miotics and anti-cholinergics, anti-glaucoma compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, prostaglandins, targeting agents, neurotransmitters, proteins, cell response modifiers, and vaccines.

Imaging Agents.

As used herein, an imaging agent is an agent that emits signal directly or indirectly thereby allowing its detection in vivo. Imaging agents such as contrast agents and radioactive agents that can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide 99 mTc; imaging agents for positron-emission tomography (PET) include positron-emitting isotopes, (18)F-fluorodeoxyglucose ((18)FDG), (18)F-fluoride, copper-64, gadoamide, and radioisotopes of Pb(II) such as 203 Pb, and 11In; imaging agents for in vivo fluorescence imaging. In other embodiments, the agent to be delivered is conjugated, or fused to, or mixed or combined with an imaging agent.

Immunostimulatory Agents.

As used herein, an immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod, imidazoquinoline, resiquimod, nucleic acids comprising an unmethylated CpG dinucleotide, monophosphoryl lipid A or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

Antigens.

The antigen may be without limitation a cancer antigen, a self-antigen, a microbial antigen, an allergen, or an environmental antigen. The antigen may be peptide, lipid, or carbohydrate in nature, but it is not so limited.

Cancer Antigens.

A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)—0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T-cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

Microbial Antigens.

Microbial antigens are antigens derived from microbial species such as without limitation bacterial, viral, fungal, parasitic and mycobacterial species. As such, microbial antigens include bacterial antigens, viral antigens, fungal antigens, parasitic antigens, and mycobacterial antigens. Examples of bacterial, viral, fungal, parasitic and mycobacterial species are provided herein. The microbial antigen may be part of a microbial species or it may be the entire microbe.

Allergens.

An allergen is an agent that can induce an allergic or asthmatic response in a subject. Allergens include without limitation pollens, insect venoms, animal dander dust, fungal spores and drugs (e.g. penicillin). Examples of natural, animal and plant allergens include but are not limited to proteins specific to the following genera: Canine (*Canis familiaris*); *Dermatophagoides* (e.g. *Dermatophagoides farinae*); Felis (*Felis domesticus*); Ambrosia (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); Alder; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides*, *Juniperus virginiana*, *Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Adjuvants.

The adjuvant may be without limitation saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic) Adjuvants may be TLR ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod, resiquimod). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages. In these latter instances, the adjuvant may be incorporated or be an integral part of the nucleic acid gel and will be released as the gel is degraded.

Immunoinhibitory Agents.

As used herein, an immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Growth Factors.

The expandable device may be coated with growth factors including without limitation VEGF-A, VEGF-C P1GF, KDR, EGF, HGF, FGF, angiopoietin-1, cytokines, endothelial nitric oxide synthases eNOS and iNOS, G-CSF, GM-CSF, VEGF, aFGF, SCF (c-kit ligand), bFGF, TNF, heme oxygenase, AKT (serine-threonine kinase), HIF.alpha.(hypoxia inducible factor), Del-1 (developmental embryonic locus-1), NOS (nitric oxide synthase), BMP's (bone morphogenic proteins), SERCA2a (sarcoplasmic reticulum calcium ATPase), beta-2-adrenergic receptor, SDF-1, MCP-1, other chemokines, interleukins and combinations thereof.

Anti-Cancer Agents.

As used herein, an anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids, or epipodophyllotoxins.

Examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin (DOXIL); Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7 trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxy-phenyl)ethane, or HDBA (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-C5, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Anti-Infective Agents.

The agent may be an anti-infective agent including without limitation an anti-bacterial agent, an anti-viral agent, an anti-parasitic agent, an anti-fungal agent, and an anti-mycobacterial agent.

Anti-bacterial agents may be without limitation β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, or quinolines.

Other anti-bacterials may be without limitation Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; or Zorbamycin.

Anti-mycobacterial agents may be without limitation Myambutol (Ethambutol Hydrochloride), Dapsone (4,4'-diaminodiphenylsulfone), Paser Granules (aminosalicylic acid granules), Priftin (rifapentine), Pyrazinamide, Isoniazid, Rifadin (Rifampin), Rifadin IV, Rifamate (Rifampin and Isoniazid), Rifater (Rifampin, Isoniazid, and Pyrazinamide), Streptomycin Sulfate or Trecator-SC (Ethionamide).

Anti-viral agents may be without limitation amantidine and rimantadine, ribivarin, acyclovir, vidarabine, trifluorothymidine, ganciclovir, zidovudine, retinovir, and interferons.

Anti-viral agents may be without limitation further include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime or integrase inhibitors. Anti-fungal agents may be without limitation imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhbitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (diiodohydroxyquin)); nitrofurans (e.g., nifurtimox); diamidines (e.g., pentamidine); tetrahydropyrimidine (e.g., pyrantel pamoate); or sulfated naphthylamine (e.g., suramin).

Other anti-infective agents may be without limitation Difloxacin Hydrochloride; Lauryl Isoquinolinium Bromide; Moxalactam Disodium; Ornidazole; Pentisomicin; Sarafloxacin Hydrochloride; Protease inhibitors of HW and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aminacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; or Troclosene Potassium.

Other Agents.

The agent may be without limitation adrenergic agent; adrenocortical steroid; adrenocortical suppressant; alcohol deterrent; aldosterone antagonist; ammonia detoxicant; amino acid; amylotropic lateral sclerosis agent; anabolic; analeptic; analgesic; androgen; anesthetic; anorectic; anorexic; anterior pituitary activator; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic including β-adrenergic agonists, methylxanthines, mast cell stabilizing agents, anticholinergics, adrenocortical steroids such as glucocorticoids; anti-atherosclerotic; anticholelithic; anticholelithogenic; anticholinergic; anticoagulant; anticoccidal; anticonvulsant; antidepressant; antidiabetic; antidiarrheal; antidiuretic; antidote; antidyskinetic; anti-emetic; anti-epileptic; anti-estrogen; antifibrinolytic; antiglaucoma; antihemorrhagic; antihemorheologic; antihistamine; antihyperlipidemic; antihyperlipoproteinemic; antihypertensive; antihypotensive; anti-infective; anti-inflammatory; antikeratinizing agent; antimigraine; antimitotic; antimycotic; antinauseant; antineutropenic; antiobsessional agent; antioxidant; antiparkinsonian; antiperistaltic; antipneumocystic; antiprostatic hypertrophy agent; antiprotozoal; antipruritic; antipsoriatic; antipsychotic; antirheumatic; antischistosomal; antiseborrheic; antisecretory; antispasmodic; antithrombotic; antitussive; anti-ulcerative; anti-urolithic; appetite suppressant; blood glucose regulator; bone resorption inhibitor; bronchodilator; carbonic anhydrase inhibitor; cardiac depressant; cardioprotectant; cardiotonic; cardiovascular agent; cerebral ischemia agent; choleretic; cholinergic; cholinergic agonist; cholinesterase deactivator; coccidiostat; cognition adjuvant; cognition enhancer; conjunctivitis agent; contrast agent; depressant; diagnostic aid; diuretic; dopaminergic agent; ectoparasiticide; emetic; enzyme inhibitor; estrogen; estrogen receptor agonist; fibrinolytic; fluorescent agent; free oxygen radical scavenger; gastric acid suppressant; gastrointestinal motility effector; geriatric agent; glucocorticoid; gonad-stimulating principle; hair growth stimulant; hemostatic; herbal active agent; histamine H2 receptor antagonists; hormone; hypocholesterolemic; hypoglycemic; hypolipidemic; hypotensive; HMGCoA reductase inhibitor; impotence therapy adjunct; inflammatory bowel disease agent; keratolytic; LHRH agonist; liver disorder agent; luteolysin; memory adjuvant; mental performance enhancer; mineral; mood regulator; mucolytic; mucosal protective agent; multiple sclerosis agent; mydriatic; nasal decongestant; neuroleptic; neuromuscular blocking agent; neuroprotective; NMDA antagonist; non-hormonal sterol derivative; nutrient; oxytocic; Paget's disease agent; plasminogen activator; platelet activating factor antagonist; platelet aggregation inhibitor; post-stroke and post-head trauma agents; progestin; prostaglandin; prostate growth inhibitor; prothyrotropin; psychotropic; radioactive agent; relaxant; rhinitis agent; scabicide; sclerosing agent; sedative; sedative-hypnotic; selective adenosine Al antagonist; sequestering agents; serotonin antagonist; serotonin inhibitor; serotonin receptor antagonist; steroid; stimulant; suppressant; thyroid hormone; thyroid inhibitor; thyromimetic; tranquilizer; unstable angina agent; uricosuric; vasoconstrictor; vasodilator; vulnerary; wound healing agent; or xanthine oxidase inhibitor.

In certain embodiments, provided herein is an apparatus (as shown in FIG. 3) comprising the expandable device 10 of any of the foregoing embodiments and a support member 52. A support member 52 as used herein, is a flexible element that is connected on one end to the expandable device, and optionally on the other end to a guide element 58. The support member is used to guide the expandable device to and from the body lumen during the sampling process. The support member must be flexible in order to navigate the inside of the individual's body such that it is able to deliver the expandable device to the sampling site.

The expandable device may be fixedly attached (not removable) to the support member, while in other embodiments, it is removable. The support member may be made of any material having a tensile strength sufficient to support movement of the expandable device through body lumens. Examples of material useful in the construction of a support member include but are not limited to a hydrogel, silicone, polyethylene, polypropylene, polyurethane, polycaprolactone, polytetrafluoroethylene (PTFE), copolymers, or a combination thereof. The support member may be a catheter or stylet. In some embodiments, the support member may be or may comprise a guide-wire. In some embodiments, the support member has a proximal end region and a distal end region and the expandable device (e.g., balloon) is located at the distal end region. In other embodiments, the support member comprises a guide at the distal end region.

Figure 3A:
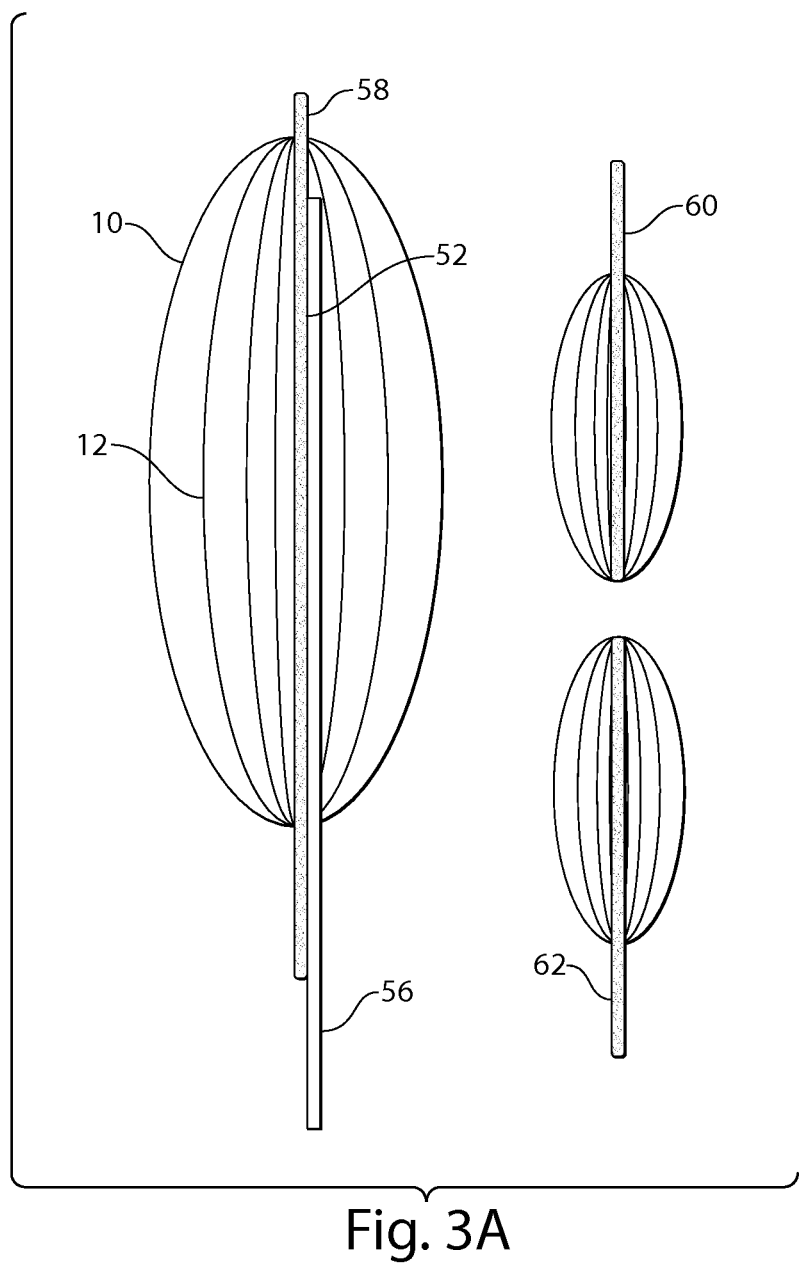
FIGS. 3A-3B schematize embodiments of the device in the deflated configuration, having a solid support member (FIG. 1B), and in the inflated configuration, having a perforated support member (FIG. 3B).

In certain embodiments, the support member exceeds the length of the expandable device. For instance, the support member may extend beyond both the proximal and distal ends of the device (FIG. 3A, left panel). In some embodiments, the expandable device is attached (fixedly or removably) to the proximal end of the support member such that the distal end 60 of the support member extends beyond the expandable device (FIG. 3A, top right panel). Alternatively, the expandable device may be attached (fixedly or removably) to the distal end of the support member such that that proximal end 62 of the support member 52 extends beyond the expandable device 10 (FIG. 3A, bottom left panel). The distance between the proximal end region and the distal end region of the support member (length) can vary greatly, as long as it is within a range useable in a human body. For instance, the length may be about 2 cm to 40 cm, 5 to 20 cm, or 5 cm to 15 cm. In particular embodiments, the distance is about 10 cm.

The device has an expanded (inflated) configuration and a contracted (deflated) configuration. The device may also assume an intermediate configuration. When deployed at a tissue collection site, the device can be partially expanded or fully expanded. In its fully expanded state, the internal and external folds are no longer pleated. Other than with self expanding devices, the apparatus will involve a mechanism for expanding the device. It typically is expanded using a gas or liquid.

In order to achieve this, the support member may include a hollow compartment 28 for transferring a gas or liquid to the device to expand the device (FIG. 4). Examples of gases used herein include oxygen, nitrogen, carbon dioxide, and water vapor. Examples of liquids include water-based, alcohol-based, or gel-like liquids. In certain embodiments, the gas or liquid is transferred through the hollow compartment to the center of the device, thereby expanding the device as the volume of the gas or liquid increases to fill the device.

In some embodiments, the apparatus comprises an actuator at the proximal end region. An actuator refers to a device for moving or controlling movement of the expandable device or entire apparatus. The actuator may be mechanical or electrical. For example, an actuator may be used to advance the expandable device to the tissue collection site. They actuator may also be used to inflate and deflate the expandable device. In some embodiments where a protective covering is used, the actuator is used to deploy the expandable device from the protective cover. In certain embodiments, the actuator is a syringe. A syringe may be used to deliver a liquid or gas to the expandable device, thereby expanding the device, either fully or partially. The syringe may be connected with the expandable device via the support member, a catheter, or other hose. Alternatively, the movement of the expandable device may be by hand and does not employ an actuator.

FIG. 1 illustrates several embodiments of the expandable device. The expandable device 10 is shown in its deflated configuration (FIG. 1A) and in its inflated configuration (FIG. 1B). In certain embodiments, the expandable device has an internal opening 26 through which, for example, a support member or hose (e.g., catheter) is inserted. In some embodiments, the opening is at the proximal end 30, while in other embodiments, there is an opening at both the proximal and distal 32 ends. The expandable device may have multiple folds, for example, 6 folds 16, 8 folds 18, 12 folds 20, 24 folds 22, or more. In its deflated (contracted) configuration, the internal folds 14 of the device are pulled in and away from the surface of the device, while the external folds 12 remain exposed at the surface. In its inflated (expanded) configuration, the internal folds 14 of the device are forced outward (unfurled) to allow for contact with the tissue of the lumen wall.

Figures 1, 1A, 2:
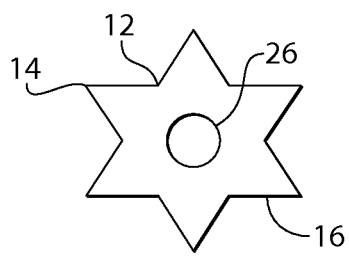
Figures 1, 1A, 2:
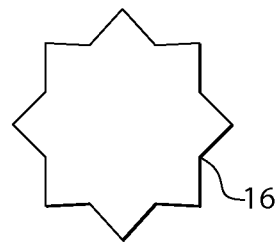
Figures 1, 1A, 2:
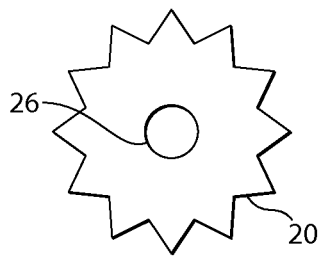
Figures 1, 1A, 2:
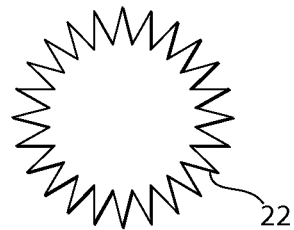
Figure 1B:
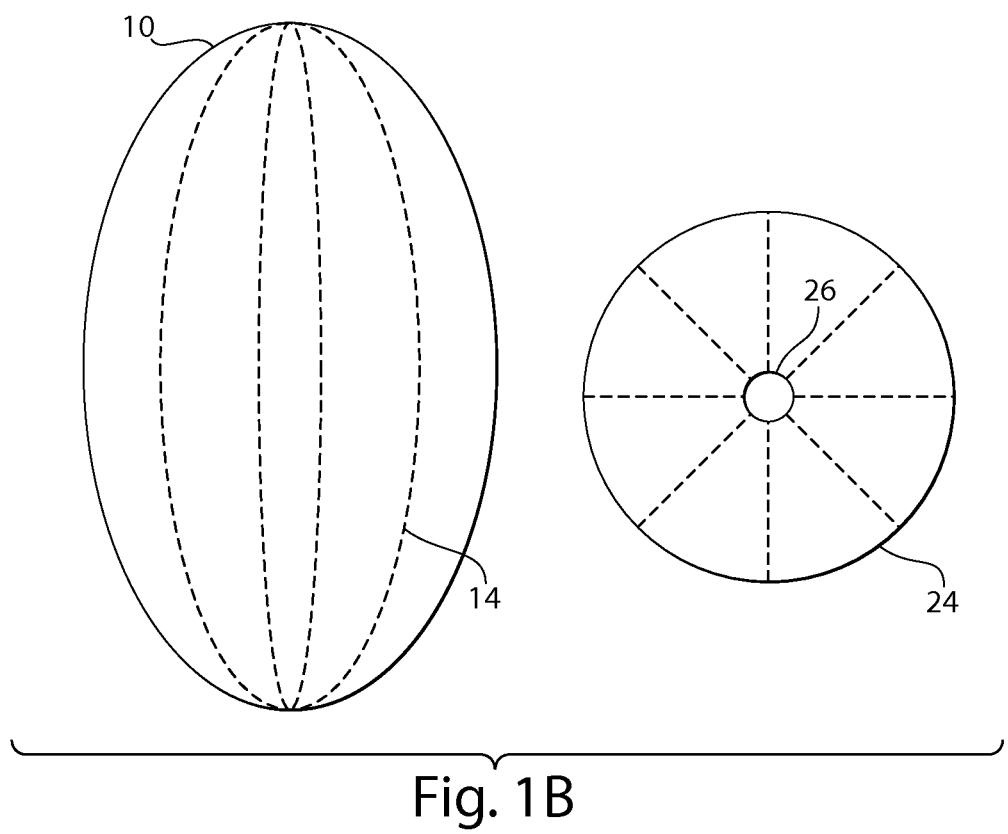

FIG. 2 illustrates one embodiment of the expandable device 10 having a tissue collection surface 60 on the surface of each internal fold 14. In its deflated configuration, the internal folds 14 are tucked between the external folds 12, and the tissue collection surface 60 is protected from exposure to the body lumen wall 100 and surrounding environment 102 (FIG. 2A). When the device 10 is expanded (e.g., fully expanded), the internal folds 14 are forced outward, placing the tissue collection surface 60 in direct contact with the internal wall (tissue) of the body lumen 100 (FIG. 2B). As the expandable device is moved (e.g., rotated or moved back and forth), the tissue is sloughed off of the lumen wall and becomes entrapped on or within the tissue collection surface 60. The expandable device is then deflated (contracted) into its corrugated, original configuration, such that the collected tissue is entrapped in the internal folds and protected from exposure to the external environment (FIG. 2A). In the instance when the tissue collection surface 60 is thicker than the expandable device material 10, for example, when the device is coated/loaded with an agent for delivery, the internal folds 14 remain tucked between the external folds 12, and the external folds 12 come together to form a seam. In this way, the agent to be delivered is sealed inside the internal folds 14 of the expandable device during protraction of the device to the tissue site of interest. At the tissue site, the device is expanded, thereby unsealing the external folds 12 and releasing the agent.

Figure 3B:
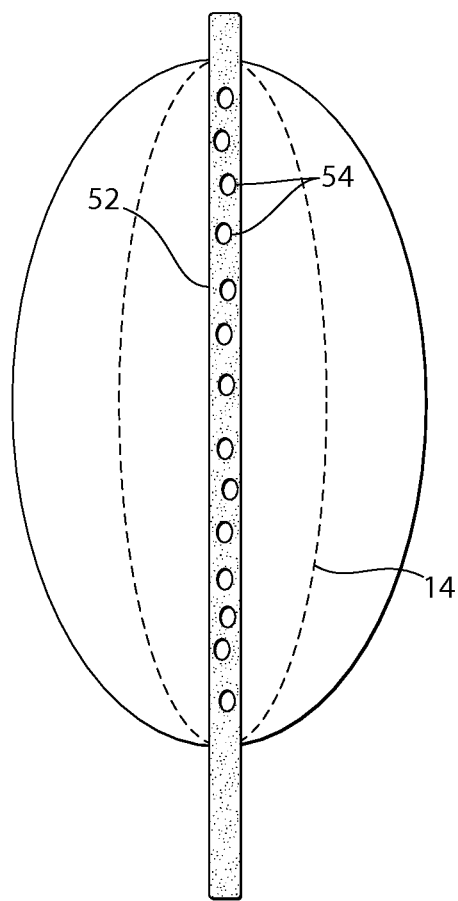

FIG. 3 illustrates an embodiment of the expandable device 10 having a support member 52 attached to the device (either fixedly or removable attached). The support member 52 may be a solid structure (FIG. 3A) or it may be perforated 54 (FIG. 3B) to allow deliver of a gas or liquid directly through the support member. In certain embodiments, deliver of a gas or liquid to the device 10 is through a hose 56 adjacent to the support member (FIG. 3A). Alternatively, in some embodiments, the hose 56 runs through the center of the support member. The hose may be perforated to allow exit of the gas or liquid, or the hose may be open-ended within the device. As described above, the support member may be positioned anywhere along the length of the support member, for example, at the proximal (FIG. 3A, top left panel) or distal (FIG. 3A, bottom left panel) end.

FIG. 4 illustrates an embodiment of the expandable device 10 having a protective covering 120. During delivery of the device 10 to a body lumen, the device is in its deflated configuration, situated within a protective covering 120 (FIG. 4A). At the site of tissue collection, the protective covering 120 is retracted, or alternatively, the device 10 is advanced, separating the device 10 from the covering 120. In certain embodiments, the device is self-expanding so that when it is removed from the protective covering, it expands, thereby forcing the internal folds 14 outward and into contact with the tissue of the lumen wall. In other embodiments, as the device is separated from the protective covering, the device 10 is inflated by delivery of a gas or liquid. The delivery of the gas or liquid may be directly through a support member 52 or through a hose 56, as described above.

FIG. 5 illustrates one particular embodiment of a cytology apparatus described herein. The apparatus includes an expandable device 10 attached to a support member 52, a hose 56 attached to the support member 52 at its proximal end (relative to the body lumen opening) and, optionally, to a connector (e.g. valve) 84 at its proximal end, and a syringe 80 and plunger 82 attached to the hose 56 via as second connector 86. Prior to advancement, the plunger 82 is used to backfill the syringe 80 with a gas or liquid, then the syringe is attached to the hose 56 via the connector 86. Prior to advancement of the device 10 into a body lumen, the distal end of the hose 56 is joined to the proximal end of the support member 52 via a connector 84. Alternatively the hose is connected to the support member, either by slipping the proximal end opening of the support member 52 over the distal end of the hose 56 to form a seal, or by slipping the distal end opening of the hose 56 over the proximal end opening of the support member 52.

The connected device 10 and hose 56 are then advanced into the lumen to the tissue collection site, guided by the distal end of the support member 52 or by a guide wire (or by the device 10 itself). The skilled artisan may use any method of determining the position of the tissue collection site known in the art (e.g., via fiber optics, dye-based imaging). Once the device 10 is positioned at the tissue collection site, the plunger 82 is slowly actuated, thereby releasing the gas or liquid such that it travels through the hose 56 to the support member 52. In certain embodiments, the support member 52 is perforated, allowing the gas or liquid to be released into the expandable device 10, thereby filling and inflating the device 10 such that the internal folds 14 unfurl permitting contact of the tissue collection surface with the wall of the lumen. The device 10 is then moved (e.g., rotated or moved back and forth), dislodging and collecting a tissue sample from the lumen wall. After the sample is collected, the device 10 is deflated by retracting the plunger 82, thereby drawing out the gas or air used to inflate the device. The device 10 and hose 56 are then carefully removed from the lumen.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Each of the foregoing patents, patent applications and references is hereby incorporated by reference.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of collecting tissue from an individual, comprising:
   (a) advancing a deflated expandable device having internal and external folds and a tissue collection surface on one or more of the internal folds to a collection site within a body lumen of an individual;
   (b) expanding the expandable device at the collection site to unfurl at least some of the folds so that the tissue collection surface contacts tissue of the body lumen;
   (c) collecting tissue on the tissue collection surface of the expandable device; wherein the step of collecting tissue involves rotating the expandable device;
   (d) contracting the expandable device; and
   (e) removing the contracted expandable device from the individual.

2. The method of claim 1, wherein the body lumen is selected from the group consisting of pharynx, larynx, oropharynx, nasopharynx, nasal cavity, nose, throat, trachea, and esophagus.

3. The method of claim 1, wherein the expandable device is a balloon.

4. The method of claim 3, wherein the balloon is partially inflated or fully inflated at the collection site.

5. The method of claim 3, wherein the step of collecting tissue involves inflating and deflating the balloon, rotating the fully inflated balloon, and/or moving the fully inflated balloon up and down.

6. A method of collecting tissue from an individual, comprising:
   (a) advancing a deflated expandable device having internal and external folds and a tissue collection surface on one or more of the internal folds to a collection site within a body lumen of an individual;
   (b) expanding the expandable device at the collection site to unfurl at least some of the folds so that the tissue collection surface contacts tissue of the body lumen;
   (c) collecting tissue on the tissue collection surface of the expandable device;
   (d) contracting the expandable device; and
   (e) removing the contracted expandable device from the individual, wherein the contracted expandable device is removed from the individual without a stent or protective cover.

7. The method of claim 6, wherein an agent is delivered to the individual prior to, at the same time as or after contracting the expandable device.

8. The method of claim 7, wherein the agent is coated on the surface of the expandable device.

9. The method of claim 8, wherein the agent is coated on the internal folds of the expandable device.

10. The method of claim 7, wherein the agent is a therapeutic agent, diagnostic agent, or imaging agent.

11. A method of collecting tissue from an individual, comprising:
    (a) advancing a deflated expandable device having internal and external folds and a tissue collection surface on one or more of the internal folds to a collection site within a body lumen of an individual;
    (b) expanding the expandable device at the collection site to unfurl at least some of the folds so that the tissue collection surface contacts tissue of the body lumen;
    (c) collecting tissue on the tissue collection surface of the expandable device;
    (d) contracting the expandable device; and
    (e) removing the contracted expandable device from the individual, wherein the expandable device is attached to a tube or channel, and wherein an instrument is advanced through the tube or channel prior to, at the same time as or after contracting the expandable device.

12. The method of claim 11, wherein the instrument is a laser fiber, a cytology brush, an applicator, a needle, forceps, or a blade.

13. A method of collecting tissue from an individual, comprising:
    (a) advancing a deflated expandable device having internal and external folds and a tissue collection surface on one or more of the internal folds to a collection site within a body lumen of an individual;
    (b) expanding the expandable device at the collection site to unfurl at least some of the folds so that the tissue collection surface contacts tissue of the body lumen;

(c) collecting tissue on the tissue collection surface of the expandable device;
(d) contracting the expandable device; and
(e) removing the contracted expandable device from the individual, wherein the expandable device is attached to a tube or channel, and wherein an agent is delivered to the individual through the tube or channel.

\* \* \* \* \*